(12) United States Patent
McMinn

(10) Patent No.: US 9,974,657 B2
(45) Date of Patent: May 22, 2018

(54) FEMORAL HEAD RESURFACING IMPLANT

(71) Applicant: Derek James Wallace McMinn, West Midlands (GB)

(72) Inventor: Derek James Wallace McMinn, West Midlands (GB)

( * ) Notice: Subject to any disclaimer, the term of this patent is extended or adjusted under 35 U.S.C. 154(b) by 0 days. days.

(21) Appl. No.: 14/722,221

(22) Filed: May 27, 2015

(65) Prior Publication Data

US 2016/0113771 A1    Apr. 28, 2016

(30) Foreign Application Priority Data

Oct. 23, 2014 (GB) .................................. 1418880.9

(51) Int. Cl.
*A61F 2/36* (2006.01)
*A61F 2/30* (2006.01)
*A61F 2/46* (2006.01)

(52) U.S. Cl.
CPC ........ *A61F 2/3603* (2013.01); *A61F 2/30724* (2013.01); *A61F 2002/30245* (2013.01); *A61F 2002/30299* (2013.01); *A61F 2002/30649* (2013.01); *A61F 2002/4631* (2013.01)

(58) Field of Classification Search
CPC .................................. A61F 2/36; A61F 2/3603
See application file for complete search history.

(56) References Cited

U.S. PATENT DOCUMENTS

| 3,925,824 | A | * | 12/1975 | Freeman | .................... | A61F 2/32 |
| | | | | | | 623/23.12 |
| 4,035,848 | A | * | 7/1977 | Wagner | .................. | A61F 2/3603 |
| | | | | | | 623/23.12 |
| 4,123,806 | A | * | 11/1978 | Amstutz | .................... | A61F 2/32 |
| | | | | | | 623/22.39 |
| 4,224,699 | A | * | 9/1980 | Weber | .................... | A61F 2/3603 |
| | | | | | | 623/23.14 |

(Continued)

FOREIGN PATENT DOCUMENTS

| EP | 0485326 A1 | 5/1992 |
| EP | 2095794 A1 | 9/2009 |
| WO | 2007/066156 A1 | 6/2007 |

OTHER PUBLICATIONS

Search Report issued in a corresponding United Kingdom Application No. GB1418880.9 dated Mar. 27, 2015.

*Primary Examiner* — Thomas J Sweet
*Assistant Examiner* — Melissa Hoban
(74) *Attorney, Agent, or Firm* — Morgan, Lewis & Bockius LLP

(57) ABSTRACT

A femoral head resurfacing implant is described comprising an external articulating surface and an internal fixation surface. A stem projects from the center of the internal fixation surface. The internal fixation surface comprises a top surface, surrounding and substantially orthogonal to a long axis of the stem, a chamfer surface extending downwardly and outwardly from the top surface and a side surface extending substantially parallel to the long axis of the stem.

(Continued)

At least one projection is arranged on the internal fixation surface to provide a predetermined gap between the top surface and/or chamfer surface and a resected head onto which the implant is to be fitted. Furthermore, the side surface constitutes or comprises a cement containment feature configured to restrict or eliminate outflow of cement from the predetermined gap.

17 Claims, 4 Drawing Sheets

(56) References Cited

U.S. PATENT DOCUMENTS

| | | | | |
|---|---|---|---|---|
| 4,312,079 | A * | 1/1982 | Dorre | A61B 17/1668 606/179 |
| 4,328,593 | A * | 5/1982 | Sutter | A61F 2/3603 623/23.42 |
| 4,332,036 | A * | 6/1982 | Sutter | A61F 2/3603 606/179 |
| 4,904,263 | A * | 2/1990 | Buechel | A61F 2/3603 623/23.44 |
| 4,955,919 | A * | 9/1990 | Pappas | A61F 2/34 623/22.26 |
| 5,133,769 | A | 7/1992 | Wagner et al. | |
| 5,405,403 | A * | 4/1995 | Mikhail | A61F 2/3609 606/66 |
| 6,063,124 | A * | 5/2000 | Amstutz | A61F 2/34 623/22.21 |
| 6,096,084 | A * | 8/2000 | Townley | A61F 2/32 623/23.12 |
| 6,156,069 | A * | 12/2000 | Amstutz | A61B 17/15 623/22.11 |
| 8,152,855 | B2 * | 4/2012 | Tulkis | A61B 17/1668 606/104 |
| 2003/0130741 | A1 * | 7/2003 | McMinn | A61B 17/1617 623/23.14 |
| 2005/0033447 | A1 * | 2/2005 | Evans | A61B 17/175 623/23.12 |
| 2008/0004710 | A1 * | 1/2008 | Ledger | A61F 2/3603 623/23.13 |
| 2008/0200991 | A1 * | 8/2008 | Collins | A61F 2/3603 623/23.12 |
| 2008/0221700 | A1 * | 9/2008 | Howald | A61B 17/175 623/23.12 |
| 2008/0262626 | A1 * | 10/2008 | Raugel | A61F 2/30734 623/22.15 |
| 2009/0149965 | A1 * | 6/2009 | Quaid | A61B 17/1668 623/22.4 |
| 2009/0192620 | A1 * | 7/2009 | Ebbitt | A61F 2/3603 623/18.11 |
| 2009/0248170 | A1 * | 10/2009 | Tuke | A61B 17/175 623/23.11 |
| 2010/0298944 | A1 * | 11/2010 | Bishop | A61B 17/1659 623/18.11 |
| 2014/0316531 | A1 * | 10/2014 | Klinger | A61F 2/3603 623/22.12 |

* cited by examiner

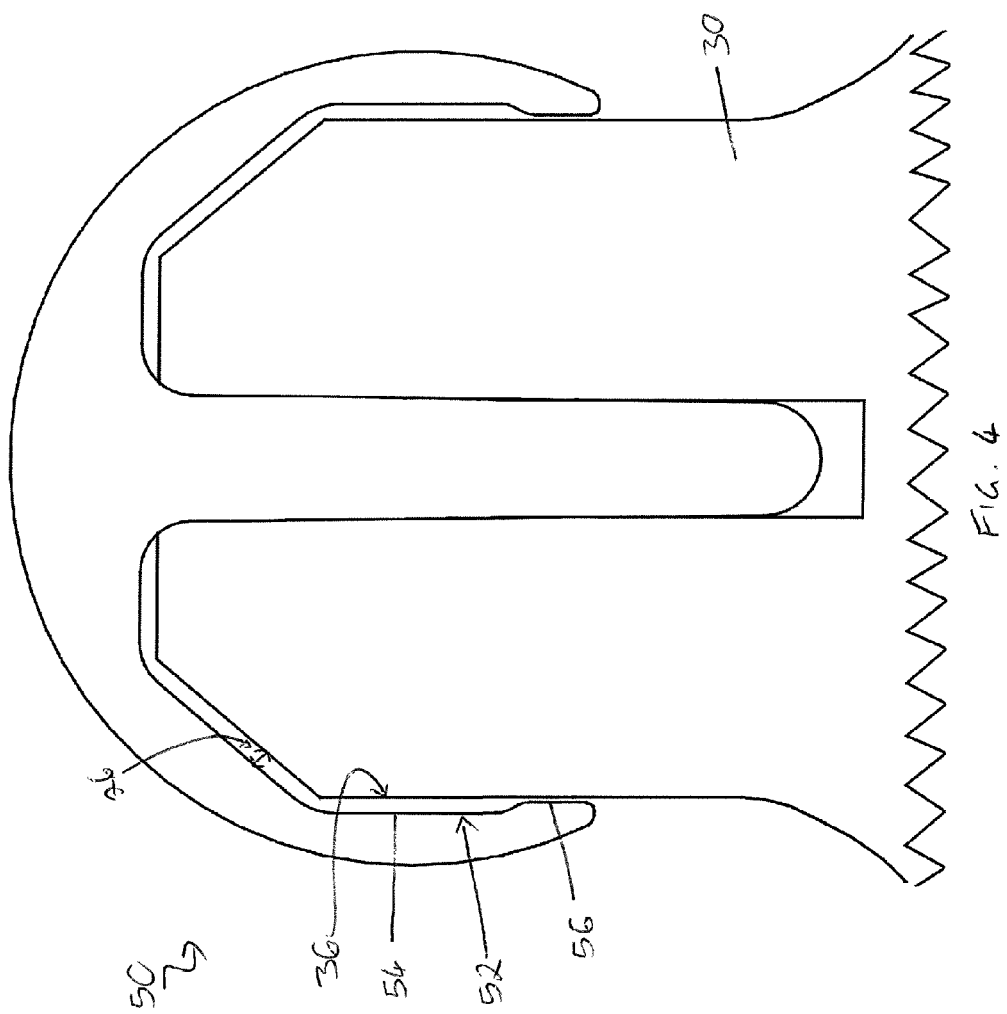

FEMORAL HEAD RESURFACING IMPLANT

RELATED APPLICATION

This application claims priority to United Kingdom Patent Application No. 1418880.9, filed on Oct. 23, 2014, the entire disclosure of which is incorporated by reference herein.

FIELD OF THE INVENTION

The present invention relates to a femoral head resurfacing implant used to resurface a partially resected femoral head.

BACKGROUND TO THE INVENTION

Traditional total hip replacements involve inserting a stem of a femoral implant into the medullary canal of a patient's femur after the femur has been resected at the distal end of the femoral neck. The stem is usually tapered such that its sides gradually converge from a wider proximal end to a narrower distal end. This configuration allows the stem to fill the majority of the medullary canal as the femur gradually narrows in a distal direction and this helps to anchor the implant in the femur. A rounded tip is provided at the distal end of the stem and a femoral neck and head is provided at the proximal end. The femoral head is constituted by a spherical ball configured for location within a corresponding acetabular cup.

In recent years, more conservative approaches, such as hip resurfacing, have been employed rather than total hip replacement as described above. In this case, the aim is to save as much healthy bone as possible and so the femur is preferably resected towards the proximal end of the femoral neck or even through the lower portion of the femoral head. The femoral head of the implant in the later case comprises a part-spherical exterior surface (configured for location within a corresponding acetabular cup) and an interior surface shaped to locate the femoral head on the remaining resected bone of the femur. This generally requires that the stem is relatively narrow at its proximal end so that there is room for sufficient healthy bone to be received within the profile of the femoral head to secure it in place. However, this configuration does not allow the stem to fill the majority of the medullary canal to anchor the implant in the femur and so cement is used to secure the femoral head on the femur.

Currently two diverging ideas lie behind the cement fixation of hip resurfacing femoral components.

The CONSERVE® Plus Total Resurfacing Hip System (C+) has a designed in 1 mm gap all around between the femoral head bone and the inside of the prosthetic component. For all prosthetic components fixed with cement a 1 mm cement mantle between the prosthetic component and the bone is often considered ideal for load transfer from the implant to the bone. High viscosity cement is intended for use in fixation of the C+ component. The cement is applied to the femoral head bone and an external pressurizing device (balloon type) is used to attempt to force cement into the bone (for micro-interlocking therewith) before insertion of the implant. The implant is then held in place on the femoral head until the cement has set (which takes approximately 12 minutes) before the femoral head is reduced into the acetabular component. In use, a major deficiency of the C+ system is medium and long term loosening of the femoral component.

The Birmingham Hip Resurfacing (BHR) component is designed to have no gap, with intended line-to-line contact, between the inside surfaces of the femoral component and the femoral head bone. In this case, low viscosity cement is used, no external pressurizing device is employed, and immediately following insertion of the BHR on the resected femur, the femoral component is reduced into the acetabular component before cement setting thereby not increasing the time taken for the operative procedure.

In use, loosening of the femoral component of the BHR is exceedingly rare. As the component is impacted into position, cement is driven into the bone of the femoral head giving excellent micro-interlock fixation. However retrieval evidence shows that large quantities of cement can be driven into the femoral head bone and rare instances of thermal necrosis of the femoral head bone have been described. This is a complication of an exothermic reaction due to cement setting made worse when large quantities of cement fill or substantially fill the femoral head bone.

Experience with fixing prosthetic components using bone cement over the past 50 years has shown that micro-interlock of cement into the spaces in cancellous bone is the desirable objective in order to achieve durable long-term component fixation. Between 1 mm and 3 mm of cement penetration into cancellous bone is usually considered ideal.

Three conditions for cement micro-interlock exist:

1) Suitable bone preparation. It is usual to prepare the surface of cancellous bone with pulsatile fluid lavage (usually saline) and brushing. Fat and other soft tissue are removed from the bone surface to allow cement to easily penetrate into spaces present in the cancellous bone.

2) Ideally low viscosity cement is used as this will easily penetrate into the cancellous bone spaces. However, a low viscosity cement must be contained as otherwise it will run out losing all potential for micro-interlock and leading to component loosening over time. For example, if low viscosity cement were used in the C+ component, the low viscosity cement would run out of the sidewall gap leading to certain component loosening. For this reason high viscosity cement, which does not run out, is used with the C+ implant. However, high viscosity cement has a lower potential to achieve cancellous bone micro-interlock. Some surgeons who use the C+ implant attempt to use low viscosity cement with an external pressurizing device to achieve bone micro-interlock, then they wait for partial cement curing (setting) allowing the cement to reach a higher viscosity state before femoral component insertion. This requires very precise timing by the surgeon and if the cement is allowed to cure too much the component cannot be inserted; too little curing and the cement runs out losing all fixation.

3) Pressure must be applied to the low viscosity cement in order to induce flow of cement into the cancellous bone spaces. In femoral head resurfacing this pressure can either be applied by an external pressurizing device or by using the component design in conjunction with the reproducible bone cuts from the usual (known art) size specific resurfacing bone cutting instruments. In the bone preparation of the femoral head for a 50 mm component, different instruments are used from those used for bone preparation of a size 48 mm or a size 52 mm component. An external pressuring device is awkward for the surgeon to use, is expensive and requires considerable surgeon skill and patience to achieve the desired objective.

It is therefore an aim of the present invention to provide an improved femoral head resurfacing implant which ameliorates some or all of the above-mentioned problems.

SUMMARY OF THE INVENTION

According to a first aspect of the present invention there is provided a femoral head resurfacing implant comprising an external articulating surface and an internal fixation surface; a stem projecting from the center of the internal fixation surface; and the internal fixation surface comprises a top surface, surrounding and substantially orthogonal to a long axis of the stem, a chamfer surface extending downwardly and outwardly from the top surface and a side surface extending substantially parallel to the long axis of the stem; wherein at least one projection is arranged on the internal fixation surface to provide a predetermined gap between the top surface and/or chamfer surface and a resected head onto which the implant is to be fitted.

Embodiments of the present invention therefore provide a femoral head resurfacing implant which is configured to maintain a predetermined gap superiorly to provide an appropriate cement mantle between a resected femoral head and a top and/or chamfer surface. This ensures that the implant does not bottom out on the bone and inadvertently drive an overly large quantity of cement into the femoral head on impaction and therefore the risk of thermal necrosis of the femoral head bone is reduced.

Notably, the side surface may constitute or comprise a cement containment feature configured to restrict or eliminate outflow of cement from the predetermined gap. For example, the side surface may be manufactured to be at or near zero degrees (e.g. angled inwardly by 0.1 degrees) with respect to the long axis of the stem. This may enable the use of low viscosity cement which is preferred for maximum bone micro-interlock without the risk of component loosening (e.g. due to an inadequate amount of cement being retained for fixation) but, at the same time, may allow for some cement to escape to prevent overfilling of the femoral head bone with cement.

The cement containment feature may be configured for line contact with the resected head so as to minimize or prevent cement from running out of the implant while it is being fitted. The cement containment feature may also serve to pressurize the cement against the internal fixation surface so as to cause a moderate portion of the cement to penetrate into the femoral head to produce a desirable level of micro-interlock thereto.

In embodiments of the invention, the side surface will be configured to provide a side gap with the resected femoral head which is smaller than the predetermined gap between the top surface and/or chamfer surface and the resected head due to the presence of the at least one projection.

In use, low viscosity cement will be poured into the internal fixation surface before the implant is impacted into position on the prepared femoral head. Advantageously, the implantation technique is quick, simple and easily reproducible for the surgeon since it does not require precise timing or an external pressurizing device to ensure the cement is adequately retained.

In certain embodiments, a plurality of projections may be provided. The projections may be equally spaced around the internal fixation surface. The at least one projection may comprise a rib, nodule, stud, ridge, ring or other protuberance.

The at least one projection may comprise a relatively large generally planar top surface, particularly suitable for a polymer or ceramic femoral component.

In certain embodiments, the at least one projection may also serve as an anti-rotation member in the cement.

The predetermined gap may be approximately 1 mm. However, depending on the properties (e.g. viscosity) of the cement employed, the predetermined gap may, for example, be 0.5 mm, 1.5 mm or 2 mm. Similarly, the side surface may be configured to provide a side gap with the resected bone that takes into account the properties of the cement. For example, if very low viscosity cement (like milk) is employed a side gap of less than 0.1 mm may be desirable; if a slightly higher viscosity cement (like single cream) is employed a side of 0.1 to 0.3 mm may be desirable; and if a more viscous cement (like double cream) is employed a side gap of 0.3 to 0.6 mm may be desirable. However, in all cases, the side gap is preferably smaller than the predetermined (superior) gap between the top/chamfer surface and bone.

If a particular manufacturer of femoral components such as ceramic manufacturers were supplying different orthopedic companies with femoral components all having the same design (according to an embodiment of the present invention), the orthopedic company could optimize the side gap to suit the particular type of cement that they sell by designing the implant and the dimensions of that particular orthopedic company's bone cutting instruments to result in a side gap optimized to their particular type of cement. Furthermore, computer modeling techniques, such as Computational Fluid Dynamics (CFD), may be used in designing the side gap for a particular type of (e.g. low viscosity) cement.

The at least one projection may be provided on the chamfer surface.

The top surface may be connected to the chamfer surface by a first concavely curved surface. Similarly, the chamfer surface may be connected to the side surface by a second concavely curved surface. These features represent good manufacturing practice since providing all internal connecting surfaces with a radius helps to ensure a smooth transition between the surfaces and improves manufacturing tolerances.

It is noted that, with the BHR component (with intended line-to-line contact between all internal surfaces and the femoral head bone) the connecting radius between the side surface and the chamfer surface can encroach on the bone pinching or crushing the bone and thus eliminating any route of escape for pressurized cement—thereby contributing to cement overfilling. With the proposed design the desired radius (i.e. second concavely curved surface) between the side surface and the chamfer surface can be accommodated in the predetermined gap between the chamfer surface and the bone such that a narrow cement escape path can be maintained between the side surface and the resected bone.

It is intended that the femoral head bone will be prepared with standard size specific instruments prior to the fitting of the femoral head resurfacing implant.

It will be understood that embodiments of the invention can enable a surgeon to reduce the femoral head resurfacing implant into an acetabular component before cement setting; can achieve moderate (ideal) cement micro interlock into the femoral head bone for durable long term component fixation; can achieve a desired predetermined (e.g. 1 mm) cement mantle between the implant and bone superiorly for optimum compressive load transfer between the implant and the bone; can avoid cement overfilling of the femoral head bone; and can negate the need for an external cement pressurizing apparatus during surgery.

The stem may comprise a rounded tip for insertion into a femur, during use. The stem may taper inwardly in a distal direction. The stem may be substantially straight. The top surface may be connected to the stem by a third concavely curved surface.

It is known to exclude cement from the bone implant interface between the stem of a resurfacing femoral component and the bone of the femoral head and neck. A slightly tapered stem inserted into a slightly undersized prepared bone cavity precludes cement from this interface. Also a relatively large radius (constituted by the third concavely curved surface) between the stem and the top surface results in a tight press fit of the stem in the near or substantially parallel-sided prepared bone cavity to, again, exclude cement from entering the stem/bone interface. This tight fit of the stem in the bone of the head & neck also serves to impart initial stability of the component on the bone and when combined with the at least one projection resting on the bone, imparts enough stability to allow the femoral component to be reduced into the acetabular component before cement setting. In addition to reducing operative time, this manoeuvre also helps to dissipate heat from the normal exothermic reaction of setting bone cement as heat is dissipated to the acetabular component and surrounding soft tissue. Another advantage of the at least one projection is that the third concavely curved surface is prevented from being forced too far into the prepared cavity for the stem.

The external articulating surface may be part-spherical and configured to be received within a corresponding acetabular cup.

The implant may be formed from any suitable material, for example, metal (e.g. cobalt chromium alloy, titanium or stainless steel), ceramic (e.g. alumina), ceramicised metal (e.g. surface oxidized zirconium alloy) or polymer (e.g. PEEK).

According to a second aspect of the present invention there is provided a hip resurfacing prosthesis comprising a femoral head resurfacing implant according to the first aspect of the present invention and an acetabular cup configured to receive the articulating surface of said femoral head resurfacing implant.

BRIEF DESCRIPTION OF THE DRAWINGS

By way of example only, specific embodiments of the present invention are described in more detail below with reference to the accompanying drawings, in which:

FIG. 4 shows a longitudinal cross-sectional view through a femoral head resurfacing implant according to a second embodiment of the present invention, with a different sidewall configuration.

DETAILED DESCRIPTION OF CERTAIN EMBODIMENTS

Figure 1:
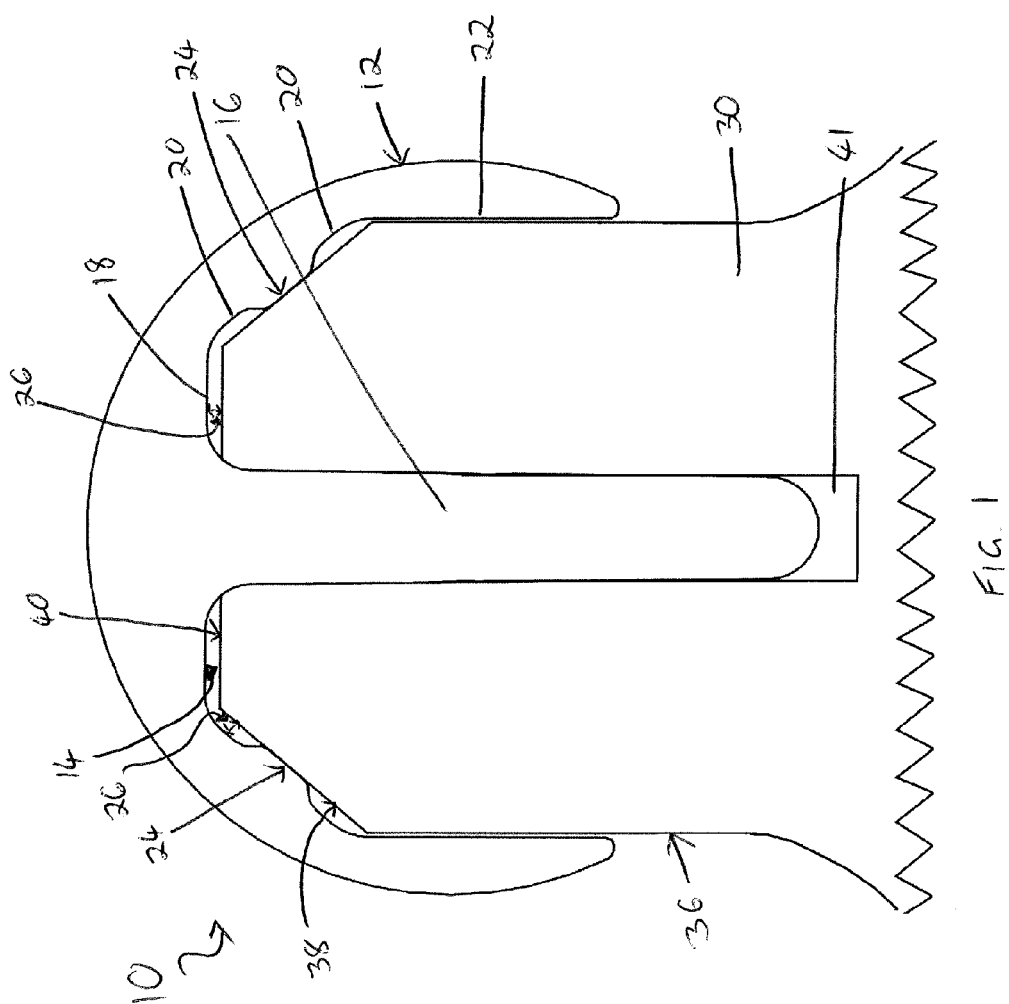
FIG. 1 shows a longitudinal cross-sectional view through a femoral head resurfacing implant according to a first embodiment of the present invention, showing two opposed projections resting on a prepared femoral head bone.
Figure 2:
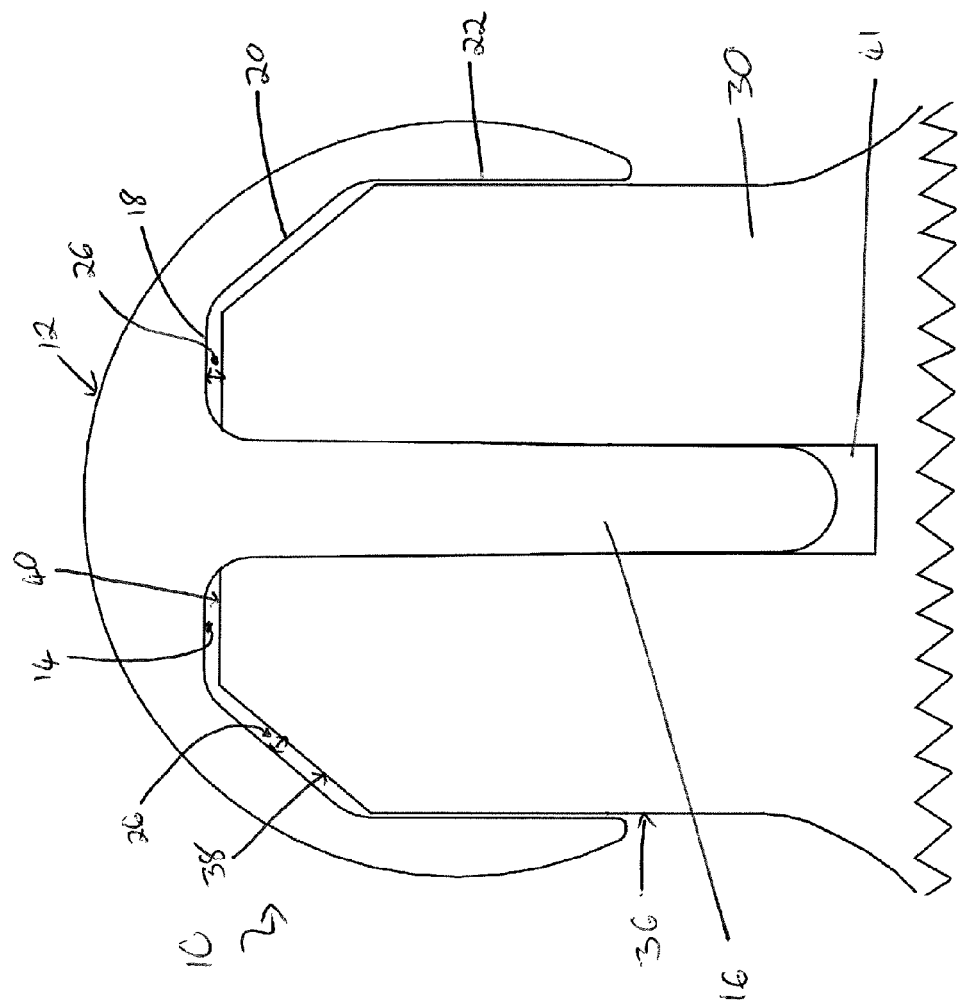
FIG. 2 shows a longitudinal cross-sectional view through the femoral head resurfacing implant of FIG. 1 but wherein the section is taken through a space between the projections.
Figure 3:
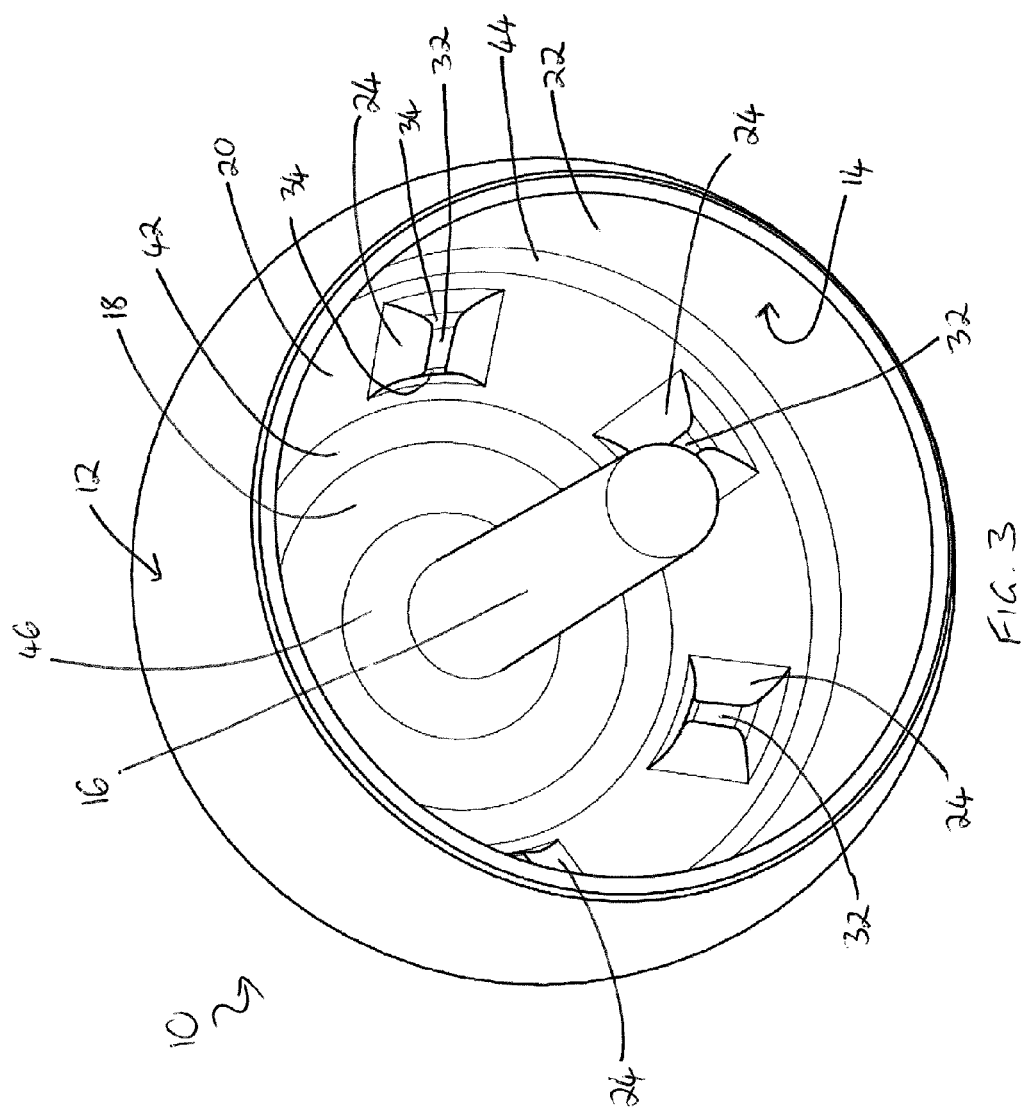
FIG. 3 shows an end isometric view of the implant of FIGS. 1 and 2.

With reference to FIGS. 1, 2 and 3, there is illustrated a femoral head resurfacing implant 10 according to a first embodiment of the present invention. The implant 10 comprises an external articulating surface 12 and an internal fixation surface 14. A stem 16 is provided which projects from the center of the internal fixation surface 14. Furthermore, the internal fixation surface 14 comprises a top surface 18, surrounding and substantially orthogonal to a long axis of the stem 16, a chamfer surface 20 extending downwardly and outwardly from the top surface 18 and a side surface 22 extending substantially parallel to the long axis of the stem 16 and constituting a cement containment feature. There are also six projections 24 arranged on the chamfer surface 20 to provide a predetermined gap 26 (in this case of 1 mm) between the top surface 18 and chamfer surface 20 and the resected head 30 onto which the implant is to be fitted.

As best shown in FIG. 3, the six projections 24 are equally spaced around the chamfer surface 20 and each projection 24 is generally in the shape of a truncated pyramid which has a generally planar flat top surface 32 which is elongate in distal direction. The proximal and distal ends 34 of each flat surface 32 are curved so as not to provide any sharp edges adjacent to the resected head 30. In use, each flat surface 32 serves as a stable support surface to maintain the predetermined gap 26 during insertion and use of the implant 10. The spacing between each projection 24 allows cement to substantially fill the predetermined gap 26 to secure the implant 10 on the resected head 30.

As shown, the resected head 30 is provided with a standard side cut 36, chamfer cut 38, top cut 40 and elongate bone cavity 41 (for receipt of the stem 16).

The top surface 18 is connected to the chamfer surface 20 by a first concavely curved surface 42. Similarly, the chamfer surface 20 is connected to the side surface 22 by a second concavely curved surface 44 and the top surface 18 is connected to the stem 16 by a third concavely curved surface 46.

In use, a low viscosity cement (not shown) is applied to the top surface 18 and chamfer surface 20. Initially, the cement will surround the projections 24 and cover the flat surfaces 32. The implant 10 will then be inserted onto the resected head 30 such that the stem 16 extends into the cavity 41, the side surface 22 forms a side gap of less than 0.6 mm with the side cut 36 (in some cases, preferably, less than 0.1 mm) and the flat surfaces 32 of the projections will be brought into contact with the chamfer cut 38 to maintain the predetermined gap 26 which will be filled with cement. The excess cement (i.e. that initially covering the flat surfaces 32) will preferentially be contained by the presence of the much narrower side gap such that the majority of the excess cement will be driven into the cancellous bone of the resected head 30. However, some egress of cement may be permitted through the small side gap to prevent overfilling of the resected head 30 with cement.

FIG. 4 shows a variant of the above embodiment in which like reference numerals will be used where appropriate. The implant 50 of FIG. 4 is substantially as described above and includes projections (not shown) to maintain the predetermined gap 26, however, in this instance, the side surface 52 comprises an upper section 54 and a lower section 56 constituting a cement containment feature. The lower section 56 is effectively a shorter version of the side surface 22 above, in that it is configured to provide a side gap of less than 0.6 mm with the side cut 36 (in some cases, preferably, less than 0.1 mm). The upper section 54 effectively extends the predetermined 1 mm gap partially down the side of the resected head 30 to provide a larger surface area for the cement mantle for optimum fixation. The lower section 56 therefore serves to substantially contain and pressurize the cement in the larger area gap 26 above, while allowing some egress to prevent overfilling.

It will be understood that embodiments of the present invention variously provide for an improved femoral implant which overcomes many of the problems encountered in relation to traditional hip replacement and hip resurfacing techniques. In particular, aspects of the present invention provide an improved fixing of the implant in the femur and a reduced risk of thermal necrosis.

It will be appreciated by persons skilled in the art that various modifications may be made to the above embodiments without departing from the scope of the present invention. For example, features from one embodiment may be mixed and matched with features from other embodiments.

The invention claimed is:

1. A femoral head resurfacing implant comprising:
an external articulating surface and an internal fixation surface;
a stem projecting from the centre of the internal fixation surface;
wherein the internal fixation surface comprises a top surface, surrounding and substantially orthogonal to a long axis of the stem, a chamfer surface extending downwardly and outwardly from the top surface and a side surface extending substantially parallel to the long axis of the stem; and
wherein at least one projection is arranged on the internal fixation surface to provide a predetermined gap between at least one of the top surface or the chamfer surface and a resected head onto which the implant is to be fitted; and
wherein the side surface constitutes or comprises a cement containment feature configured to restrict or eliminate outflow of cement from the predetermined gap; and
wherein the side surface is configured to provide a side gap with the resected femoral head which is smaller than the predetermined gap between the at least one of the top surface or the chamfer surface and the resected head; and
wherein the at least one projection is provided on the top surface or the chamfer surface and comprises a planar top parallel to the top surface or the chamfer surface on which the at least one projection is provided; and
wherein at least one void is provided adjacent the at least one projection and adjacent the top surface or the chamfer surface on which the at least one projection is provided such that, in use, cement fills the at least one void to provide fixation between the top surface and the resected head and the chamfer surface and the resected head.

2. The implant according to claim 1 wherein the side surface is at or near zero degrees with respect to the long axis of the stem.

3. The implant according to claim 1 wherein the side surface is angled inwardly by approximately 0.1 degrees with respect to the long axis of the stem.

4. The implant according to claim 1 wherein a plurality of projections is provided.

5. The implant according to claim 4 wherein the projections are equally spaced around the internal fixation surface.

6. The implant according to claim 1 wherein the at least one projection comprises a rib, nodule, stud, ridge, ring or other protuberance.

7. The implant according to claim 1 wherein the at least one projection serves as an anti-rotation member in the cement.

8. The implant according to claim 1 wherein the predetermined gap is approximately 0.5 mm, 1 mm, 1.5 mm or 2 mm.

9. The implant according to claim 1 wherein the side gap provided by the side surface is less than 0.1 mm, less than 0.3 mm, or less than 0.6 mm.

10. The implant according to claim 1 wherein the at least one projection is provided on the chamfer surface.

11. The implant according to claim 1 wherein a concavely curved surface is located between the top surface and the chamfer surface.

12. The implant according to claim 1 wherein a concavely curved surface is located between the top surface and the stem.

13. The implant according to claim 1 wherein the external articulating surface is part-spherical and is configured to be received within a corresponding acetabular cup.

14. The implant according to claim 1 formed from metal, ceramic, ceramicised metal or polymer.

15. The implant according to claim 1 wherein a concavely curved surface is located between the chamfer surface and the side surface.

16. The implant according to claim 15 wherein below the concavely curved surface the side surface is projection-free.

17. A hip joint prosthesis comprising a femoral head resurfacing implant according to claim 1 and an acetabular cup configured to receive the articulating surface of said femoral head resurfacing implant.

* * * * *